United States Patent
Liu

(10) Patent No.: US 10,085,715 B2
(45) Date of Patent: Oct. 2, 2018

(54) ULTRASONIC SCANNING SYSTEM

(71) Applicant: QISDA CORPORATION, Taoyuan (TW)

(72) Inventor: Chun-Cheng Liu, Hsinchu (TW)

(73) Assignee: Qisda Corporation, Taoyuan (TW)

( * ) Notice: Subject to any disclaimer, the term of this patent is extended or adjusted under 35 U.S.C. 154(b) by 595 days.

(21) Appl. No.: 14/718,111

(22) Filed: May 21, 2015

(65) Prior Publication Data

US 2016/0120504 A1     May 5, 2016

(30) Foreign Application Priority Data

Oct. 30, 2014    (TW) .............................. 103137686 A

(51) Int. Cl.
| | |
|---|---|
| A61B 8/00 | (2006.01) |
| A61B 5/053 | (2006.01) |
| A61B 5/0488 | (2006.01) |
| A61B 8/14 | (2006.01) |
| A61B 5/0402 | (2006.01) |
| A61B 8/08 | (2006.01) |

(52) U.S. Cl.
CPC .......... *A61B 8/4416* (2013.01); *A61B 5/0402* (2013.01); *A61B 5/0488* (2013.01); *A61B 5/0537* (2013.01); *A61B 8/0866* (2013.01); *A61B 8/14* (2013.01); *A61B 8/4444* (2013.01); *A61B 8/463* (2013.01); *A61B 8/5284* (2013.01); *A61B 8/56* (2013.01)

(58) Field of Classification Search
None
See application file for complete search history.

(56) References Cited

U.S. PATENT DOCUMENTS

| | | | | |
|---|---|---|---|---|
| 5,078,149 A | * | 1/1992 | Katsumata | A61B 8/4281 600/459 |
| 5,669,393 A | * | 9/1997 | Faisandier | A61B 5/00 600/509 |
| 5,749,833 A | * | 5/1998 | Hakki | A61B 5/042 600/380 |
| 6,007,372 A | * | 12/1999 | Wood | G01S 19/13 439/502 |
| 2004/0059205 A1 | * | 3/2004 | Carlson | A61B 5/0006 600/310 |
| 2005/0049517 A1 | * | 3/2005 | Mathew | A61B 5/0488 600/546 |

(Continued)

FOREIGN PATENT DOCUMENTS

| | | |
|---|---|---|
| CN | 103565475 A | 2/2014 |
| JP | 2005270375 A | 10/2005 |

OTHER PUBLICATIONS

English translation of JP 2005-270375.*

*Primary Examiner* — Pascal M Bui Pho
*Assistant Examiner* — Bradley Impink

(57) ABSTRACT

An ultrasonic scanning system includes a host device, an ultrasonic probe, and at least two electrodes. The ultrasonic probe is electrically connected to the host device for performing an ultrasonic scanning operation toward a detecting region to generate a scanning signal and to transmit the scanning signal to the host device. The at least two electrodes are disposed on the ultrasonic probe and are connected to the host device for detecting a physiological signal of the detecting region and transmitting the physiological signal to the host device.

8 Claims, 5 Drawing Sheets

(56) References Cited

U.S. PATENT DOCUMENTS

| | | | | |
|---|---|---|---|---|
| 2005/0245839 A1* | 11/2005 | Stivoric | .............. | G06F 19/3418 600/549 |
| 2005/0267597 A1* | 12/2005 | Flaherty | ............... | A61B 5/0031 623/24 |
| 2012/0325586 A1* | 12/2012 | Meggs | ................. | A61G 7/1042 182/231 |
| 2013/0213399 A1* | 8/2013 | Hansmann | ........... | A61B 5/7203 128/204.23 |

* cited by examiner

ULTRASONIC SCANNING SYSTEM

BACKGROUND OF THE INVENTION

1. Field of the Invention

The present invention relative to an ultrasonic scanning system, and more specifically, to an ultrasonic scanning system disposing at least two electrodes on an ultrasonic probe to detect a physiological signal.

2. Description of the Prior Art

With development of medical technology, an ultrasonic scanning device has been widely applied to medical examination for performing an ultrasonic scanning operation on a specific body region of a subject (e.g. a pregnant woman or a patient) and then generating ultrasonic scanning images for a medical personnel (e.g. a doctor) to view, so that the medical personnel could know the health condition (e.g. a fetus growth condition or an internal organ pathology condition) of the subject.

However, if the medical personnel wants to further detect a physiological signal (e.g. an electrocardiogram signal, an electromyography signal, or body fat) of the subject, an additional signal transmitting cable with electrodes needs to be connected to the ultrasonic scanning system in advance for allowing the medical personnel to attach the electrodes to a detecting region on the subject's body, so as to cause a time-consuming and strenuous detecting and wiring process. The aforesaid problem causes the medical personnel much inconvenience in detecting physiological signals.

SUMMARY OF THE INVENTION

The present invention provides an ultrasonic scanning system including a host device, an ultrasonic probe, and at least two electrodes. The ultrasonic probe is electrically connected to the host device for performing an ultrasonic scanning operation toward a detecting region to generate a scanning signal and transmitting the scanning signal to the host device. The at least two electrodes are disposed on the ultrasonic probe and are connected to the host device for detecting a physiological signal of the detecting region and transmitting the physiological signal to the host device.

The present invention further provides an ultrasonic scanning system including a host device, an ultrasonic probe, and at least two electrodes. The ultrasonic probe has an ultrasonic signal detecting surface. The at least two electrodes are disposed on the ultrasonic probe. The ultrasonic signal detecting surface and the at least two electrodes are used to contact a detecting region simultaneously for selectively performing an ultrasonic scanning operation on the detecting region to generate a scanning signal and detecting a physiological signal of the detecting region. The cable is electrically connected to the host device, the ultrasonic probe, and the at least two electrodes. The ultrasonic probe selectively transmits the scanning signal and the physiological signal of the detecting region to the host device via the cable.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
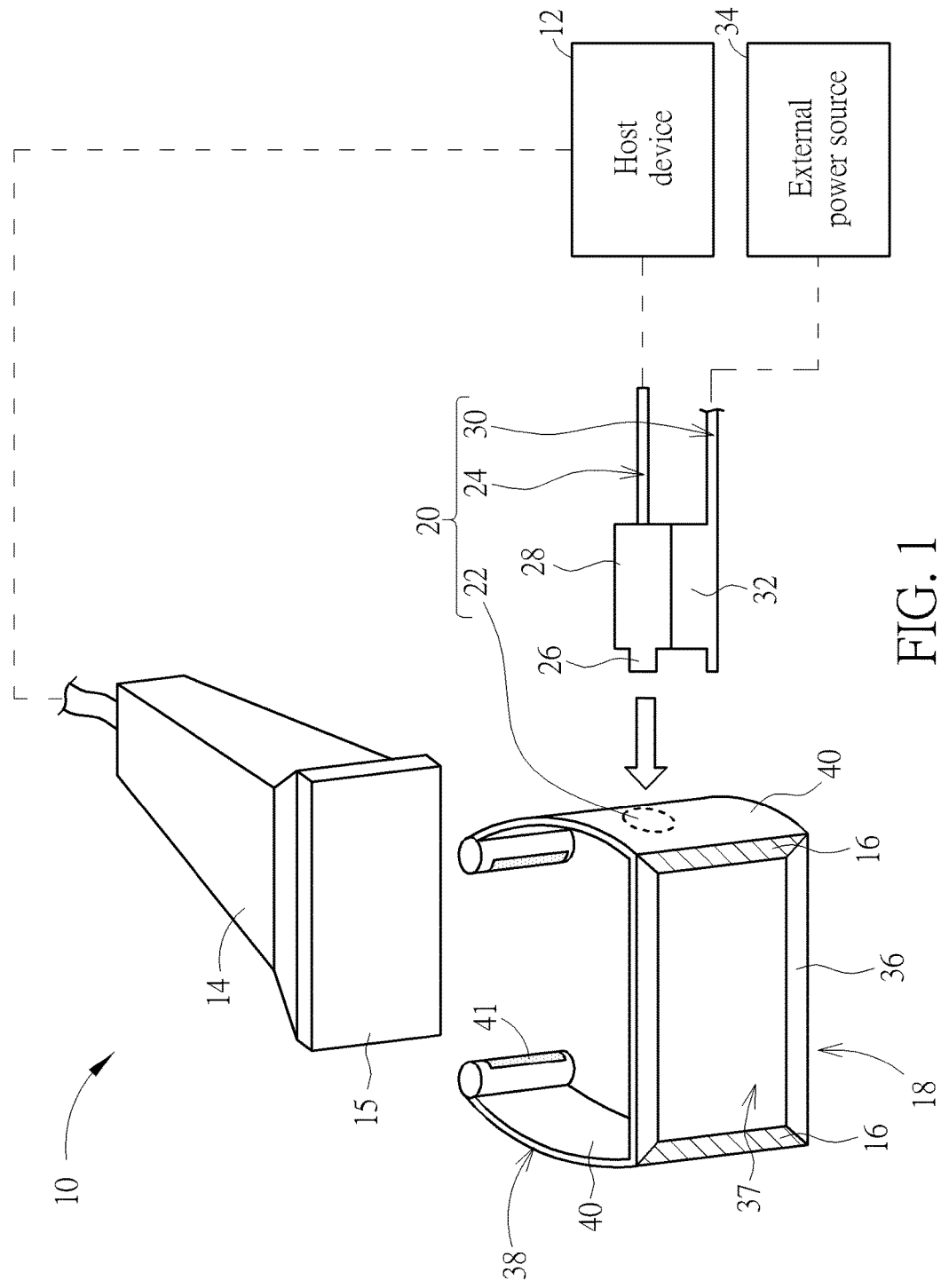
FIG. 1 is a diagram of an ultrasonic scanning system according to an embodiment of the present invention.
Figure 2:
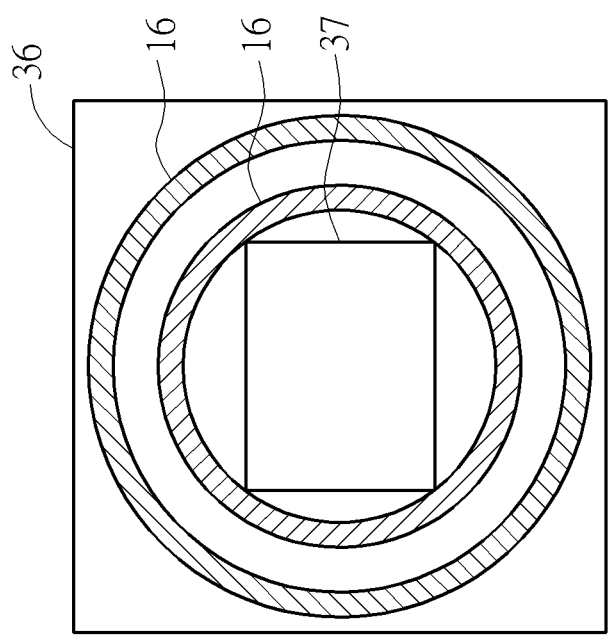
FIG. 2 is a diagram of two electrodes being disposed on a frame portion according to another embodiment of the present invention.

Please refer to FIG. 1, which is a diagram of an ultrasonic scanning system 10 according to an embodiment of the present invention. As shown in FIG. 1, the ultrasonic scanning system 10 includes a host device 12, an ultrasonic probe 14, at least two electrodes 16 (two shown in FIG. 1, but not limited thereto), and a sleeving member 18. The host device 12 could be a conventional ultrasonic scanning host to display a scanning signal generated by the ultrasonic probe 14 for a user (e.g. a doctor) to view and then make a corresponding diagnosis. The ultrasonic probe 14 is electrically connected to the host device 12 for performing an ultrasonic scanning operation on a detecting region (e.g. a surface region on a subject's body) and then transmitting a corresponding scanning signal to the host device 12, so that the host device 12 could display a corresponding scanning result. The electrodes 16 are disposed on the ultrasonic probe 14 and electrically connected to the host device 12. Each electrode 16 could be in a strip shape, but not limited thereto. For example, in another embodiment, the electrodes 16 could be in a circular shape and disposed on the ultrasonic probe 14 in a concentric circular arrangement (as shown in FIG. 2). The electrodes 16 could be used for detecting a physiological signal of a detecting region scanned by the ultrasonic probe 14 and then transmitting the detected physiological signal back to the host device 12. The host device 12 could display the scanning signal and the physiological signal on the same display screen, utilize two display devices to respectively display the scanning signal and the physiological signal, or only display the scanning signal and calculate related data according to the physiological signal by other application software. The physiological signal detected by the electrodes 16 could be an electrocardiogram signal, an electromyography signal, or a body resistance signal (e.g. body fat), but not limited thereto, meaning that the electrode 16 could also adopt other electrode detecting method to detect other type of physiological signal (e.g. a respiratory signal).

In practical application, the electrodes 16 could be electrically connected to the host device 12 in a wired or wireless manner. For example, as shown in FIG. 1, the ultrasonic scanning system 10 could further include a signal transmitting device 20. The signal transmitting device 20 is disposed on the sleeving member 18 and electrically connected to the electrodes 16. To be more specific, in this embodiment, the signal transmitting device 20 adopts a wired transmission design and includes a connection port 22 (briefly depicted by dotted lines in FIG. 1) and a signal transmitting cable 24. The connection port 22 is disposed on the sleeving member 18 and electrically connected to the electrodes 16. The signal transmitting cable 24 could have a plug 26 and be electrically connected to the host device 12. Accordingly, the plug 26 could establish signal transmission between the host device 12 and the electrodes 16 for transmitting a physiological signal detected by the electrodes 16 after being inserted into the connection port 22. Furthermore, in this embodiment, the plug 26 could have an active amplification unit 28 for amplifying a physiological signal detected by the electrodes 16, so as to help a user make a more correct diagnosis. To be noted, if the host device 12 has no power source disposed thereon to provide the active amplification unit 28 with electrical power, the signal transmitting device 20 could further include a power cable 30. The power cable 30 could have a connection socket 32 and be electrically connected to an external power source 34. Accordingly, the active amplification unit 28 could be inserted into the connection socket 32 to establish power connection between the external power source and the active amplification unit 28, so that the active amplification unit 28 could perform a signal amplification operation.

Furthermore, in another embodiment, the signal transmitting device 20 could adopt a wireless transmission design. In brief, the signal transmission device 20 could be a wireless transmitting unit and could utilize the aforesaid power supply design to establish power transmission between the signal transmission device 20 and an external power source. Moreover, instead of an external power source, the wireless transmitting unit could also utilize a standard battery, a button cell battery, or a lithium battery for power supply. Accordingly, the signal transmitting device 20 could be wirelessly connected to the host device 12 to establish wireless signal transmission between the host device 12 and the electrodes 16.

As for the structural design of the sleeving member 18, as shown in FIG. 1, the sleeving member 18 could have a frame portion 36 and an arm portion 38. The frame portion 36 has an opening 37 to expose an ultrasonic signal detecting surface 15 of the ultrasonic probe 14. The two electrodes 16 are attached to the frame portion 36 respectively. The arm portion 38 extends from the frame portion 36 toward the ultrasonic probe 14 and is detachably connected to the ultrasonic probe 14. The ultrasonic signal detecting surface 15 and the two electrodes 16 could simultaneously contact a surface of a detecting region detected by the ultrasonic probe 14. To be more specific, in this embodiment, the arm portion 38 could have at least two elastic arms 40 (two shown in FIG. 1, but not limited thereto). The two elastic arms 40 are located at two sides of the ultrasonic probe 14 for cooperatively clamping the ultrasonic probe 14, so as to make the sleeving member 18 disposed on the ultrasonic probe 14 more steadily. Each elastic arm 40 could have an attachment end 41 to be detachably attached to the ultrasonic probe 14. A conventional attachment design could be applied to attachment between the elastic arm 40 and the ultrasonic probe 14, such as a Velcro attachment design. The advantage of utilizing the two elastic arms 40 to clamp the ultrasonic probe 14 is that the sleeving member 18 could be suitable for ultrasonic probes of different sizes.

Via the aforesaid designs, when a user moves the ultrasonic probe 14 to a detecting region of a subject (e.g. a belly region of a pregnant woman) to perform an ultrasonic scanning operation, the electrodes 16 and the ultrasonic signal detecting surface 15 of the ultrasonic probe 14 could contact a surface of the detecting region scanned by the ultrasonic probe 14 simultaneously. In such a manner, the host device 12 could display an ultrasonic scanning image (e.g. an image of a fetus) and a physiological signal diagram (e.g. an electrocardiogram or an electromyography diagram of a pregnant woman) according to a scanning signal transmitted from the ultrasonic probe 14 and a physiological signal transmitted from the electrodes 16, so as to allow the user to know a physical condition of a subject (e.g. an uterine contraction condition of a pregnant woman) while viewing the ultrasonic scanning image. Thus, the present invention could efficiently solve the prior art problem that an additional signal cable with electrodes needs to be connected to the ultrasonic scanning system in advance for detecting physiological signals to cause a time-consuming and strenuous detecting and wiring process. Accordingly, convenience of the ultrasonic scanning system 10 in detecting physiological signals could be greatly improved.

Figure 3:
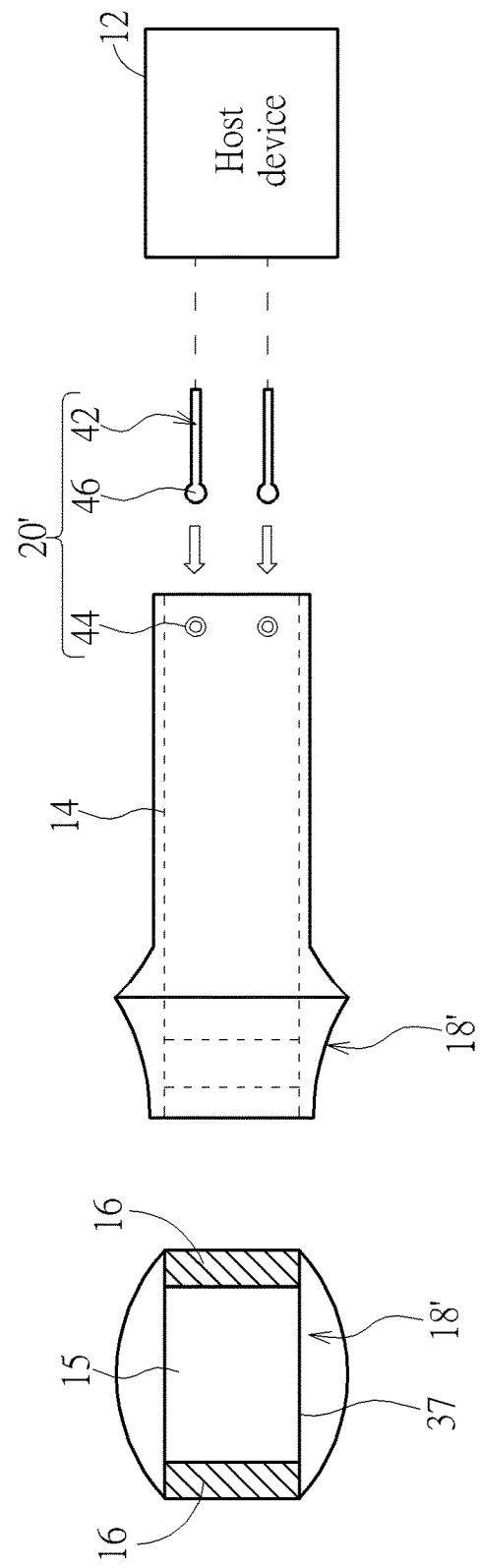
FIG. 3 is a diagram of a sleeving member being electrically connected to a host device via a signal transmitting device according to another embodiment of the present invention.

It should be mentioned that the sleeving member could be a sleeving cloth in another embodiment. For example, please refer to FIG. 3, which is a diagram of a sleeving member 18' being electrically connected to the host device 12 via a signal transmitting device 20' according to another embodiment of the present invention. Components both mentioned in this embodiment and the aforesaid embodiment represent components with similar functions or structures, and the related description is omitted herein. As shown in FIG. 3, in this embodiment, the sleeving member 18' could be a sleeving cloth. The opening 37 is formed on the sleeving cloth. The two electrodes 16 could be preferably made of conductive cloth material and disposed on the sleeving cloth adjacent to the opening 37. Cables connected to the electrodes 16 and a male buckle connection 44 are weaved in the sleeving cloth (not shown in FIG. 3). Via the aforesaid designs, the sleeving member 18' could be used for sleeving the ultrasonic probe 14 to make the ultrasonic signal detecting surface 15 exposed from the opening 37. Furthermore, this embodiment could adopt the design that the signal transmitting device 20' is electrically connected to the host device 12 in a wired manner (but not limited thereto, meaning that the signal transmitting device 20' could also adopt the wireless or wired connection design mentioned in the aforesaid embodiment). As shown in FIG. 3, the signal transmitting device 20' could include a signal transmitting cable 42, the male buckle connection 44, and a female buckle connection 46. The signal transmitting cable 42 is electrically connected to the host device 12. The male buckle connection 44 is disposed on the sleeving cloth and is electrically connected to the electrodes 16, and the female buckle connection 46 is electrically connected to the signal transmitting cable 42 (but not limited thereto, meaning that the present invention could also adopt the design that the female buckle connection 46 is disposed on the sleeving cloth and is electrically connected to the electrodes 16, and the male buckle connection 44 is electrically connected to the signal transmitting cable 42). Accordingly, the male buckle connection 44 could be used for buckling up with the female buckle connection 46 to establish signal transmission between the host device 12 and the electrodes 16.

Figure 4:
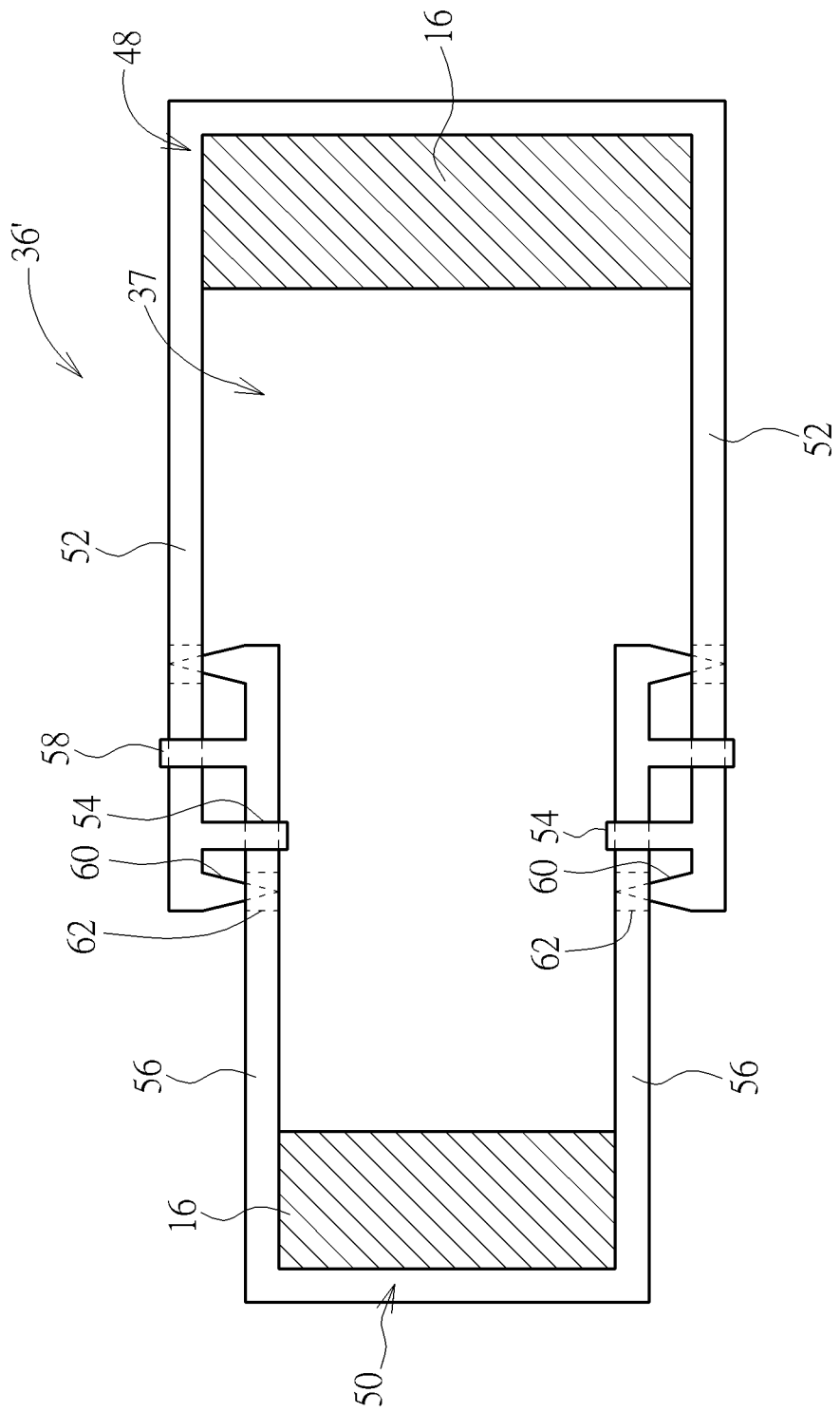
FIG. 4 is a diagram of the two electrodes being disposed on a frame portion according to another embodiment of the present invention.

Furthermore, the structural design of the frame portion of the sleeving member is not limited to the aforesaid embodiments. For example, please refer to FIG. 4, which is a diagram of the two electrodes 16 being disposed on a frame portion 36' according to another embodiment of the present invention. Components both mentioned in this embodiment and the aforesaid embodiments represent components with similar functions or structures, and the related description is omitted herein. As shown in FIG. 4, the frame portion 36' has the opening 37, a first frame structure 48, and a second frame structure 50. The two electrodes 16 are connected to the first frame structure 48 and the second frame structure 50. The first frame structure 48 is telescopically connected to the second frame structure 50 for forming the opening 37 cooperatively with the second frame structure 50. To be more specific, the first frame structure 48 could have at least one first arm portion 52 (two shown in FIG. 4, but not limited thereto) and a first ear portion 54. The second frame structure 50 could have at least one second arm portion 56 (two shown in FIG. 4, but not limited thereto) and a second ear portion 58. The first ear portion 54 extends from the first arm portion 52 toward the second arm portion 56. The second ear portion 58 extends from the second arm portion 56 toward the first arm portion 52. The first arm portion 52 could be movably disposed through the second ear portion 58, and the second arm portion 56 could be movably disposed through the first ear portion 54, so as to make the first frame structure 48 slidable relative to the second frame structure 50. Accordingly, a user could adjust an area of the opening 37 based on the practical detecting condition, so as to achieve the purpose that a distance between the two electrodes 16 could be adjustable for conforming to different detecting needs. Furthermore, in this embodiment, the first arm portion 52 could have a hook end 60. At least one engaging slot 62 (one shown in FIG. 4, but not limited thereto) is formed on the second arm portion 56 corresponding to the hook end 60. In such a manner, the hook end 60 could be used for engaging with the engaging slot 62 to fix a telescopic length of the first frame structure 48 relative to the second frame structure 50. The aforesaid design could also be applied to the second arm portion 56, and the related description could be reasoned by analogy and omitted herein.

Furthermore, the present invention could also adopt the design that the distance between the two electrodes could be adjustable by replacing the sleeving member. In brief, the ultrasonic scanning system 10 could further include another sleeving member having the same structure with the sleeving member 18 (the related description could be reasoned by analogy according to the aforesaid embodiments) to make the two electrodes 16 away from each other at different distances (e.g. an area of an opening of the aforesaid sleeving member could be different from the area of the opening 37 of the sleeving member 18). Accordingly, when the two electrodes 16 are disposed on the sleeving member 18, the two electrodes 16 could be away from each other at a first distance. On the other hand, when the two electrodes 16 are disposed on the aforesaid sleeving member, the two electrodes 16 could be away from each other at a second distance. The first distance is different from the second distance. In such a manner, a user could selectively dispose the two electrodes 16 on the aforesaid sleeving member or the sleeving member 18 according to the practical detecting condition, so as to achieve the purpose that the distance between the two electrodes 16 could be adjustable for conforming to different detecting needs.

Figure 5:
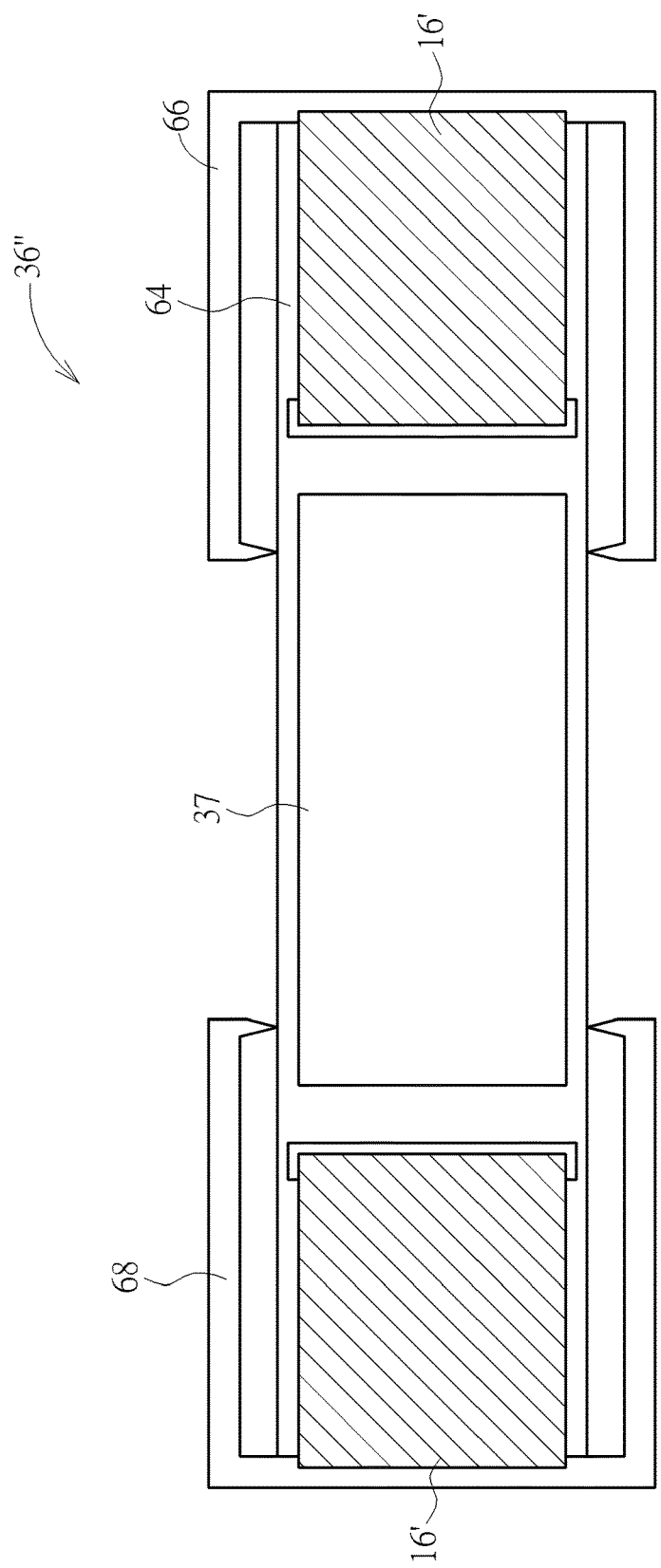
FIG. 5 is a diagram of two electrodes being disposed on a frame portion according to another embodiment of the present invention.

Furthermore, the design of the electrode is not limited to the aforesaid embodiments. For example, please refer to FIG. 5, which is a diagram of two electrodes 16' being disposed on a frame portion 36" according to another embodiment of the present invention. Components both mentioned in this embodiment and the aforesaid embodiment represent components with similar functions or structures, and the related description is omitted herein. As shown in FIG. 5, the frame portion 36" could have the opening 37, a frame body 64, a first frame structure 66, and a second frame structure 68. The opening 37 is formed on the frame body 64. The first frame structure 66 and the second frame structure 68 are movably disposed on the frame body 64 (e.g. in a clamping manner as shown in FIG. 5). The two electrodes 16' are disposed in the frame body 64 respectively in a retractable manner and are connected to the first frame structure 66 and the second frame structure 68 respectively. Accordingly, when the first frame structure 66 and the second frame structure 68 move relative to the frame body 64, the two electrodes 16' could be pulled from or pushed into the frame body 64 with movement of the first frame structure 66 and the second frame structure 68, so that a user could adjust an exposed area of each electrode 16' according to the practical detecting condition for achieving the purpose that the detecting size of the electrodes 16' could be adjustable for conforming to different detecting needs.

To be noted, the sleeving member mentioned in the aforesaid embodiments could be an omissible component. That is, the present invention could adopt the design that the electrodes are directly attached to the ultrasonic probe for simplifying the design of the ultrasonic scanning system. Furthermore, the aforesaid signal transmitting device could also be an omissible component, meaning that the ultrasonic scanning system of the present invention could utilize only one cable for signal transmission. For example, in another embodiment, the ultrasonic scanning system provided by the present invention could include a host device, an ultrasonic probe, at least two electrodes, and a cable. The cable is electrically connected to the host device, the ultrasonic probe, and the electrodes. Accordingly, the ultrasonic probe could selectively transmit a scanning signal generated from an ultrasonic signal detecting surface of the ultrasonic probe and a physiological signal detected by the electrodes to the host device via the cable, so as to simplify the signal transmitting design of the ultrasonic scanning system.

Compared with the prior art, the present invention adopts the design that the electrodes are disposed on the ultrasonic probe, to achieve the purpose that the host device could display a corresponding ultrasonic scanning image and a corresponding physiological signal diagram according to the scanning signal transmitted from the ultrasonic probe and the physiological signal transmitted from the electrodes. In such a manner, the ultrasonic scanning system provided by the present invention could allow a user to know a physical condition of a subject while viewing an ultrasonic scanning image. Thus, the present invention could efficiently solve the prior art problem that an additional signal cable with electrodes needs to be connected to an ultrasonic scanning system in advance for detecting physiological signals to cause a time-consuming and strenuous detecting and wiring process. Accordingly, convenience of the ultrasonic scanning system in detecting physiological signals could be greatly improved, so as to help a user make a more correct ultrasonic diagnosis.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An ultrasonic scanning system comprising:
a host device;
an ultrasonic probe electrically connected to the host device for performing an ultrasonic scanning operation toward a detecting region to generate a scanning signal and transmitting the scanning signal to the host device;
a first sleeving member having a frame portion and an arm portion, the frame portion having an opening to expose an ultrasonic signal detecting surface of the ultrasonic probe, the arm portion extending from the frame portion toward the ultrasonic probe and being detachably connected to the ultrasonic probe, the frame portion further having a first frame structure and a second frame structure, the first frame structure being telescopically connected to the second frame structure to form the opening cooperatively with the second frame structure, and the first frame structure being slidable relative to the second frame structure for adjusting an area of the opening; and at least two electrodes attached to the frame portion and connected to the first frame structure and the second frame structure respectively, the at least two electrodes being connected to the host device for detecting a physiological signal of the detecting region and transmitting the physiological signal to the host device.

2. The ultrasonic scanning system of claim 1, wherein the arm portion has at least two elastic arms, and the at least two elastic arms are located at two sides of the ultrasonic probe to clamp the ultrasonic probe cooperatively.

3. The ultrasonic scanning system of claim 2, wherein each elastic arm has an attachment end detachably attached to the ultrasonic probe.

4. The ultrasonic scanning system of claim 1 further comprising:
a signal transmitting device disposed on the arm portion and electrically connected to the at least two electrodes for connecting to the host device.

5. The ultrasonic scanning system of claim 4, wherein the signal transmitting device comprises:
a connection port disposed on the arm portion and electrically connected to the at least two electrodes; and
a signal transmitting cable electrically connected to the host device, the signal transmitting cable having a plug, the plug being inserted into the connection port to establish signal transmission between the host device and the at least two electrodes.

6. The ultrasonic scanning system of claim 1, wherein the first frame structure has at least one first arm portion and a first ear portion, the second frame structure has at least one second arm portion and a second ear portion, the first ear portion extends from the at least one first arm portion toward the at least one second arm portion, the second ear portion extends from the at least one second arm portion toward the at least one first arm portion, and the at least one first arm portion and the at least one second arm portion are movably disposed through the second ear portion and the first ear portion respectively so as to make the first frame structure slidable relative to the second frame structure.

7. The ultrasonic scanning system of claim 6, wherein the at least one first arm portion has a hook end, at least one engaging slot is formed on the at least one second arm portion corresponding to the hook end, and the hook end is engaged with the at least one engaging slot for fixing a telescopic length of the first frame structure relative to the second frame structure.

8. An ultrasonic scanning system comprising:
a host device;
an ultrasonic probe electrically connected to the host device for performing an ultrasonic scanning operation toward a detecting region to generate a scanning signal and transmitting the scanning signal to the host device;
a first sleeving member having a frame portion and an arm portion, the frame portion having an opening to expose an ultrasonic signal detecting surface of the ultrasonic probe, the arm portion extending from the frame portion toward the ultrasonic probe and being detachably connected to the ultrasonic probe, the frame portion further having a frame body, a first frame structure, and a second frame structure, the opening being formed on the frame body, and the first frame structure and the second frame structure being movably disposed on the frame body; and
at least two electrodes disposed in the frame body respectively in a retractable manner and connected to the first frame structure and the second frame structure respectively, the at least two electrodes being connected to the host device for detecting a physiological signal of the detecting region and transmitting the physiological signal to the host device, and the at least two electrodes being pulled from or pushed into the frame body respectively by the first frame structure and the second frame structure to adjust an exposed area of each electrode when the first frame structure and the second frame structure move relative to the frame body.

* * * * *